| United States Patent [19] | [11] Patent Number: 4,743,597 |
| Javitt et al. | [45] Date of Patent: May 10, 1988 |

[54] COMPOSITION COMPRISING AN OXYGENATED CHOLESTEROL AND USE THEREOF FOR TOPICAL TREATMENT OF DISEASES

[76] Inventors: Norman B. Javitt, 501 E. 79th St., New York, N.Y. 10021; Richard B. Stoughton, P.O. Box 1264, Rancho Sante Fe, Calif. 92067

[21] Appl. No.: 822,878

[22] Filed: Jan. 27, 1986

[51] Int. Cl.⁴ .............................................. A61K 31/56
[52] U.S. Cl. ..................................... 514/182; 514/863
[58] Field of Search ................................ 514/182, 863

[56] References Cited

U.S. PATENT DOCUMENTS

| 3,551,554 | 12/1970 | Herschler | 424/7.1 |
| 4,316,893 | 2/1982 | Rajadhyaksha | 424/180 |
| 4,427,668 | 1/1984 | Javitt | 514/182 |
| 4,432,976 | 2/1984 | Annen et al. | 514/863 X |

Primary Examiner—Leonard Schenkman
Attorney, Agent, or Firm—Ostrolenk, Faber, Gerb & Soffen

[57] ABSTRACT

The invention is directed to a pharmaceutical composition comprising an oxygenated cholesterol and a penetration-enhancing agent which is useful for topical application to the skin of a patient suffering from a proliferative skin disease characterized by geminative cells having a rapid rate of replication, e.g. psoriasis. The composition comprises an effective amount for the inhibition of germinative cell mitosis of an oxygenated cholesterol, e.g. 26-hydroxycholesterol, or a pharmaceutically effective derivative thereof e.g. an ester or ether. The invention is further directed to a method of treating a patient suffering from said skin disease comprising applying to the effected skin said therapeutic composition. The invention is also directed to the topical application of these compositions to the skin to decrease inflammation.

24 Claims, No Drawings

COMPOSITION COMPRISING AN OXYGENATED CHOLESTEROL AND USE THEREOF FOR TOPICAL TREATMENT OF DISEASES

BACKGROUND OF THE INVENTION

1. Field of the Invention

This invention relates to pharmaceutical compositions for application to the skin and to a method for the treatment of proliferative skin diseases. More particularly, this invention relates to topical compositions containing an oxygenated cholesterol, e.g. 26-hydroxycholesterol, or a pharmaceutically acceptable derivative of an oxygenated cholesterol, e.g. an ester or an ether. This invention relates, particularly, to a topical composition containing 26-hydroxycholesterol or cholest-1,4-diene-26-ol-3-one or a pharmaceutically acceptable derivative thereof and an agent for enhancing the penetration of these compounds into and through the skin.

2. Prior Art

Proliferative skin diseases are widespread throughout the world and afflict millions of humans and their domesticated animals. This invention provides a method for the treatment of such diseases and pharmaceutical compositions useful in alleviating such diseases.

As used herein, the expression "proliferative skin diseases" means benign skin diseases which are characterized by epidermal cell proliferation, or division, and may also be associated with incomplete tissue differentiation. Psoriasis is the most serious of the skin diseases with which this invention is concerned. Such diseases include: psoriasis, atopic dermatitis, nonspecific dermatitis, primary irritant contact dermatitis, allergic contact dermatitis, lamellar ichthyosis, epidermolytic hyperkeratosis, premalignant sun induced keratosis, non-malignant keratosis, and seborrheic dermatitis in humans and atopic dermatitis and mange in domesticated animals.

Heretofore, proliferative skin diseases have been generally accepted by mankind as an ongoing evil having degrees of severity variable with time, with inherited skin traits and external factors, but always have been recognized as unsightly, painful, morbid diseases. Over the history of mankind, innumerable medicines and treatments have been proposed, tried and used with varying degrees of success. However, no treatment heretofore devised or pharmaceutical compositions used has been entirely successful in the wide spectrum of specific diseases encompassed by the expression proliferative skin diseases.

The present day treatments of commercial significance which are prescribed and used for the treatment of proliferative skin diseases and associated inflammation include three approaches: (1) topical applications: coal tar derivatives, 5-fluorouracil, vitamin A acid, glucocorticoids in high dosage, bath oils and non-specific emolient creams and ointments; (2) systemic administration: glucocorticoids and classic anti-cancer agents, for example, methothrexate, hydroxyurea, azaibine, cyclophosphamide; and (3) physical modalities: ultraviolet light, irradiation, and in severe cases, surgery.

Numerous compositions are known for the treatment of skin disorders and diseases by topical application which provide, in certain cases, some remission of the original symptoms, each treatment suffers some defect, for example, temporary and incomplete mitigation of symptoms, rapid re-occurrence of the disease when mitigation is terminated, serious and sometimes irreversible damage (atrophy) resulting from the topical application for extended times of glucocorticoids, acute bone marrow suppression and cirrhosis of the liver resulting from the protracted use of methothrexate which may lead to death of the patient, and the causation of cancer by the application of anti-cancer drugs, irradiation, or ultraviolet rays.

Psoriasis is perhaps the most prevalent type proliferative skin disease. The early stage eruption of psoriasis may be non-specific in appearance and in such early stages is often confused with a variety of other skin diseases. The initial lesion is an erythematous papule which may progress to pustulation. Soon after the erythematous papules, the characteristic papulosquamous plaque appears. The typical psoriatic eruption consists of erythematous, scaling plaques of variable size. The lesions are, in most cases, symmetrical. Clinically, the scale is distinctive, silvery and luxuriant in its pristine, untreated state. Underneath is a dull red surface which, upon removal of the scale, may show fine capillary bleeding points. Always sharply limited in border and frequently clearing in the center, psoriasis may come in any size and the scale may, in turn, range from being absent to extremely thick.

Psoriasis, in addition to being an inflammatory disease, is a benign hyperplastic disease of the skin. Epidermal cells in areas of skin involvement have a very rapid rate of replication. The mitotic index of the germinative cell population per unit length of involved epidermis is increased, and there is a reduced epidermal cell transmit time, or epidermal cell "turnover" time in involved areas. Accordingly, the epidermis of the psoriatic lesion grows very fast (about ten times normal rates) and sheds large amounts of scale. This is one of the key factors in the pathology of the disease.

In view of the foregoing, the principal thrust of the treatment protocol for psoriasis centers around use of antimetabolites or nicotinamide antagonists, such as the topical application of methotrexate, and folic acid antagonist; Azaribine, an orotidylate decarboxylase inhibitor (triacetyl-6-azauridine); hydroxyurea; 6-aminonicotinamide; and systemically with mycophenolic acid. The first three drugs are antimetabolic agents and have been reported effective in producing remissions in patients with severe recalcitrant disease.

However, all of these drugs have major side effects and can be given only in very severe cases and under extremely careful supervision by those experienced in their use. In many instances, some of the adverse effects of these drugs are worse than the psoriasis, particularly when using antineoplastic agents.

In view of the foregoing, what is needed is a method for treating psoriasis by the topical application of a suitable compound to the psoriatic lesion. It would further be highly desirable to have a composition which is not only useful in the topical treatment of psoriasis, but other type proliferative diseases, preferably by antimetabolites which characteristically inhibit mitosis.

26-Hydroxycholesterol, some of its derivatives and analogs, certain properties and some uses thereof are known, for example:

Van Lier et al, Biochemistry 6, 3269 (1967) and Aringer et al. Biochem. Biophys. Acta., 665, 13 (1981) describes the finding that 26-hydroxycholesterol present in human atheromata in vivo is of enzymatic origin.

Kandutsch et al, Science 201, 498 (1978) reported that oxygenated sterols such as 25-hydroxycholesterol inhibit cholesterol synthesis in vitro.

Javitt et al, "26-Hydroxycholesterol Identification and Quantitation in Human Serum", J. Biol. Chem., 256:12644 (1981) describes the presence of 26-hydroxycholesterol (cholest-5-ene-3 beta, 26-diol) in biological fluids after neonatal life.

Javitt et al, in J. Biol. Chem., 256:12644 (1981) describes the determination of 26-hydroxycholesterol in biological fluids by GLC-MS analysis using a deuterated analog. See, also, Javitt et al, Biomedical Mass Spectrometry, 9:61-63 (1982).

U.S. Pat. No. 4,427,668 to Javitt (1984) describes a process for regulating cholesterol level in the body, particularly of tissue cholesterol, through the monitoring and/or administration of 26-hydroxycholesterol. Administration is through the use of injectables, such as intravenous injectables, utilizing conventional pharmaceutical carriers for such use in tablet, capsule, oral liquids or parenteral injectables. See also Japanese No. 58 172317 to Javitt et al which describes the use of 26-hydroxycholesterol compositions for depression of hyperplasia in smooth muscle cell.

None of these foregoing references, however, teach or suggest the use of 26-hydroxycholesterol for the topical treatment of skin disorders or diseases.

Nor does any of these references disclose a method for passing 26 hydroxycholesterol through the skin directly into the blood stream without requiring an injection through the skin.

It is therefore an object of this invention to provide a new composition and method for treating proliferative skin diseases.

Another object of the invention is to provide a method for treating proliferative skin diseases by topical application of a therapeutic composition to the effected skin area.

It is still another object of this invention to provide novel pharmaceutically acceptable compositions including an oxygenated cholesterol e.g. 26-hydroxycholesterol, or a pharmaceutically effective derivative thereof.

It is yet another object of this invention to provide cosmetic as well as therapeutic compositions containing 26-hydroxycholesterol, or its derivatives which, when topically applied, will substantially alleviate the symptoms of various inflammatory skin disorders.

It is yet another object of this invention to provide compositions for transdermal delivery of an oxygenated cholesterol to a subject.

SUMMARY OF THE INVENTION

The present invention relates to the discovery that oxygenated cholesterols, e.g. 26-hydroxycholesterol, or pharmaceutically acceptable derivatives thereof, when combined with a suitable carrier are surprisingly effective for treating proliferative skin diseases such as psoriasis and inflammatory diseases.

The invention is directed to a composition useful for topical application to the skin of a patient suffering from a proliferative skin disease characterized by germinative cells having a rapid rate of replication, said composition comprising an effective amount for the inhibition of germinative cell mitosis of 26-hydroxycholesterol or a pharmaceutically effective derivative thereof and a pharmaceutically effective carrier therefor.

The invention is further directed to a method of treating a patient suffering from a proliferative skin disease characterized by germinative cells having a rapid rate of replication, comprising applying to the effected skin a therapeutic composition comprising a therapeutically effective amount for the inhibition of germinative cell mitosis of an oxygenated cholesterol, e.g. 26-hydroxycholesterol, or a pharmaceutically effective derivative thereof and a pharmaceutically effective carrier therefor.

The invention is further directed to a therapeutic composition for topical application to the skin of a patient suffering from an inflammatory skin disease characterized by vasodilation and reddening of the skin, said composition comprising an effective amount for enhancing vasoconstriction and decreasing inflammation of the skin of an oxygenated cholesterol, e.g. 26-hydroxycholesterol or a pharmaceutically effective derivative thereof and a pharmaceutically effective carrier therefor.

Finally, this invention is directed to a method for carrying an oxygenated cholesterol, e.g. 26-hydroxycholesterol, or a pharmaceutically effective derivative thererof, through skin or other body membranes which comprises combining said oxygenated cholesterol with a penetration-enhancing compound comprising a compound having the structural formula:

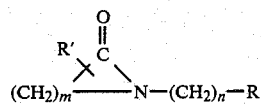

Wherin R' is H or a lower alkyl group, m is 3-7, n is 0-17 and R is —CH$_3$, phenyl or substituted phenyl or

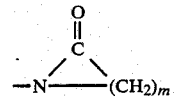

to provide a composition including an effective amount of said oxygenated cholesterol and topically applying said compositions to the skin.

DETAILED DESCRIPTION OF THE INVENTION

As reported in THE MERCK INDEX, Tenth Edition, Published by MERCK & CO., INC., Rahway, N.J. (1983) cholesterol has the following structure:

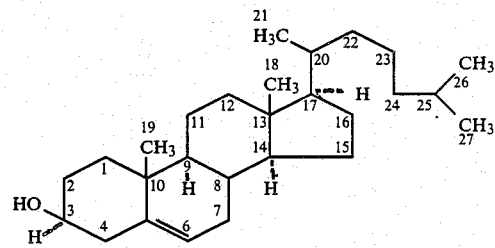

The active compound in the compositions and methods of this invention comprises an oxygenated derivative of cholesterol wherein the 26 position is substituted with a hydroxy, keto, or carboxylic acid group, i.e. the 26 position is oxidized. Other positions may also be oxidized. For example, the 3 and/or the 16 position may comprise a keto group. Preferably, the 26 position is substituted with a hydroxy group. Compounds which are within the scope of this invention include:
(1) cholest-5-ene-3-ol-26 formyl-16-one
(2) cholest-4-ene-26-ol-3-one
(3) cholest-1,4-diene-26-ol-3-one
(4) 3 keto-cholest-1,4-dien-26-oic acid
(5) cholest-5-ene-3 beta, 26-diol-16-one (26-hydroxycholesterol-16-one)
(6) cholest-4-ene-26-ol-3,16-dione
(7) cholest-1,4-diene-26-ol-3, 16-dione
(8) 3,16-diketo-cholest-1,4-dien-26-oic acid
(9) 26-hydroxycholesterol The stereo isomers of 26-hydroxycholesterol and the above-described oxygenated derivatives thereof, including the 25R and 25S stereo isomers and mixtures thereof, both naturally occurring and synthetically produced, are also within the scope of the present invention, in that they have an analogous inhibiting effect on proliferative diseases or inflammation. More preferably, the active compound is selected from the group consisting of 26-hydroxycholesterol and cholest-1,4-diene-26-ol-3-one.

The other compounds listed above, may be derived from 26-hydroxycholesterol or cholesterol by oxidation. For example, double bonds may be introduced into the A-ring and the 3-hydroxyl group oxidized to a ketone. Thus the A-ring of certain of the above compounds will have the formula:

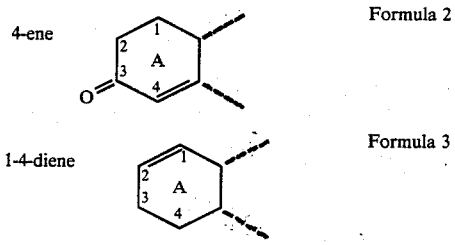

These foregoing A-ring modified compounds may be produced by Oppenauer oxidation (see "Organic Reaction in Steroid Chemistry", Vol. 1, Van Nostrand pp. 234-237, Edited by Fried and Edwards (1972, incorporated herein by reference) of the silyl ether of 26-hydroxycholesterol, which is produced by standard silation reactions. This is subsequently treated with DDQ (dichlorodicyanobenzoquinone) to introduce double bonds at the 1 and 4 positions in the A-ring (see pages 308-318 of Fried and Edwards, above).

As used herein, as a compound to be administered to a patient, the above oxygenated derivatives of cholesterol include also "pharmaceutically acceptable derivatives" thereof. For example, the mono and diesterified derivatives and mono and diether derivatives of any of the above compounds are included. Usually fatty acids, the same or analogous to those naturally occurring, are used to form the esters, but other inorganic and organic esters, such as the sulfates, carbonates and glucuronides, routinely employed in preparing pharmaceutically acceptable esters can be used. Esterification and/or etherification can occur at the 3-and/or 26-position. Aryl and/or alkyl ethers, such as methyl, ethyl, or cyclo (e.g. cyclopentyl ethers) are contemplated. Furthermore, acid salts can be used. Esterification and/or etherification can occur at the 3-and/or 26-position. Aryl and/or alkyl ethers, such as methyl, ethyl, or cyclo (e.g. cyclopentyl ethers) are contemplated. Furthermore, acid salts and various substituted compounds, for example, those containing elements such as fluorine commonly used in modification of steroid-type compounds, as long as they are pharmaceutically acceptable, can be used in the method of the present invention.

The therapeutic compositions of this invention are applied topically. The term "topical" as employed herein relates to the use of the active compound incorporated in a suitable pharmaceutical carrier, and applied at the site of the disease for exertion of local or transdermal action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oil-soluble, water-soluble or emulsion-type bases, e.g. petrolatum, lanolin, polyethylene glycols, as well as mixtures thereof.

Topical ointments can be prepared by dispersing the active compound or compounds in a suitable ointment base such as petrolatum, lanolin, polyethylene glycol, mixtures thereof, and the like. Advantageously, the active compound or compounds is finely divided by means of a colloid mill utilizing light liquid petrolatum as a lavigating agent prior to dispersal in the ointment base. Topical creams and lotions are prepared dispersing the active compound or compounds in the oil phase prior to the emulsification of the oil phase in water.

Oily components, emulsifiers, dispersing agents, gelatinizers and solid materials which can be used to prepare such formulations are well known as those used in the preparation of cosmetics and topical products. Oily components, emulsifiers, dispersing agents and gelatinizers, of course, can be used alone or in combination with each other.

It has been found that topical application with occlusion of an area larger than the medicated area produces improved results relative to nonoccluded topical applications and is, therefore, the preferred method of topical treatment with the composition of this invention.

In addition to conventional formulations, the activity of the therapeutic compositions of this invention may be substantially enhanced by the use of skin penetrating vehicles, i.e., compounds which enhance percutaneous absorption of the active compound through the skin. Vehicles which enhance the skin penetration of the active compounds disclosed herein include dimethysulfoxide (DMSO), etc. As noted above, preferably the penetration-enhancing compound is selected from the group of compounds represented by the structural formula:

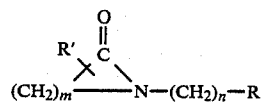

wherein R' is H or a lower alkyl group, m is 3-7, n is 0-17 and R is —CH₃, phenyl or substituted phenyl or

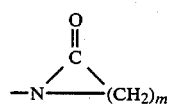

In a more preferred embodiment of the above penetration-enhancing compound when m is 3 and R is —CH₃, then n is not 0-6. These compounds are described in the aforementioned U.S. Pat. Nos. 4,424,210 and 4,316,893, the entire disclosures of which are incorporated herein by reference. The most preferred penetration-enhancing compound is AZONE, a trademarked product sold by Nelson Research & Development Company, Irvine, California. This most preferred penetration-enhancing compound, 1-dodecylazacycloheptan-2-one, is described in Stoughton, Arch. Dermatol., Vol. 118 (1982).

The amount of the composition to be administered will obviously be an effective amount for the desired result expected therefrom. This, of course, will be ascertained by the ordinary skilled practitioner. In accordance with the usual prudent formulating practices, a dosage near the lower ends of the useful range of the particular agent may be employed initially and the dosage increased as indicated from the observed response, as in the routine procedure of the physician.

The compositions of this invention comprise a pharmaceutical carrier and about 0.1% to 10% and preferably 1% to 5% by weight of the active compound relative to the total weight of the composition.

If the amount of the active compound or its derivatives used is too low, the desired results of this invention will not be obtained or obtained insufficiently. The use of more of said active compound than required will not improve the desirable results in a manner proportional to the amount of compound used, and might bring about undesirable effects. For this reason, the above-mentioned range is preferred.

Preferably, the active compound (which is generally difficult to dissolve in many otherwise suitable pharmaceutical carriers) is utilized with the aforementioned penetration-enhancing compounds, which is from 0.1% to 10% and preferably 1% to 5% by weight relative to the total weight of the topical composition of this invention.

In carrying out the novel method employing the topical composition, the active compound formulated, for example, as an ointment or solution, is applied to the affected area of the skin at a rate varying from about 0.1 mg/sq. cm of skin surface per day up to 10 mg./sq. cm of skin surface per day until the appearance of the affected skin has returned to normal. The ointment or solution is generally applied for several days and in the case of psoriasis, preferably using a continuous occlusive dressing. The concentration of active ingredients can vary from about 0.1% to about 10% by weight of the composition applied. With the foregoing concentration, a dose of about 0.01 ml/sq. cm of skin surface should supply an amount of active compound sufficient to achieve a desirable effect.

The dosage of topical composition and length of time required for successfully treating each individual patient may vary, but those skilled in the art of medicine will be able to recognize these variations and adjust the course of therapy accordingly.

One or more drugs selected from antibiotics, antihistiminics, antimycotic agents and vitamins may be incorporated into the compositions of this invention to prepare a compounded preparation.

In accordance with this invention, it has been found that proliferative skin diseases and associated inflammation are alleviated, that is the symptoms of the disease are noticeabley improved or become undetectable, by the treatment of the afflicted patient, or animal, with one or more of the pharmaceutical compositions described in detail herein.

A proliferative skin disease can be considered to be effectively treated when there is a noticeable decrease in the thickness of a lesion to palpation, with or without residual redness, or residual slightly dilated blood vessels or residual hyper- or hypo-pigmentation. For example, psoriasis has been effectively treated when a scale-free psoriasis lesion is noticeably decreased in thickness, or noticeably but incompletely cleared or completely cleared. These effective treatments are all characterized by an inhibition of mitosis of the germinative cells.

By the use of the term "germinative cells" herein, it is meant the innermost layer of epidermal cells, which undergo mitosis.

Additionally, the compositions of this invention may also be used to treat other skin disorders such as keratinizations and inflammatory diseases such as dry skin, ichthyosis, palmar and plantar hyperkeratosis, dandruff, acne, Darier's disease, pruritis, lichen simplex chronicus, keratoses, warts, herpes, and eczema. Generally, this is accomplished by effecting vasomotor activity.

Although the biochemical mechanism by which the active compound is effective for treating skin diseases and disorders is not fully understood, it is believed that the active compound may inhibit the activity of HMG Co A reductase, the rate limiting enzyme for the production of several compounds for cell growth, by reducing the amount of enzyme produced. This biological reaction would inhibit the mitosis of the generative cells.

It has also been shown that 26-hydroxycholesterol is metabolized to bile acids by the liver. It is theorized that the extended side chain of these biologically active steroids, in contrast to currently available glucocorticoids for the treatment of skin disorders, results in metabolism by the liver. Thus, there is no interference with adrenal hormone synthesis and metabolism, reducing a major side effect of currently available glucocorticoids.

The following examples identify certain compositions which typify the manner of combining selective active compounds with a pharmaceutical carrier for use in the process of treatment of proliferative skin diseases as above generally described, but they are not intended to represent the limits of either the compositions or of the process of this invention which is defined in the claims.

EXAMPLE 1

500 milligrams of 26-hydroxycholesterol is dissolved in 0.4 milliliter of AZONE with heating (80° C.) and then diluted with 9.6 milliliters of ethanol to produce 10 ml. of ethanol solution containing 4% of AZONE and 5% of 26-hydroxycholesterol. This method is used to prepare ethanol solutions comprising 5 percent 26-hydroxycholesterol and 4 percent AZONE and 1 percent 26-hydroxycholesterol and 1 percent AZONE. Solutions of 16-ketocholesterol, cholest-1,4-diene-26-ol-3-one are also prepared by this method. The solutions are evaluated for vasoconstricting activity as reported in EXAMPLE 2.

EXAMPLE 2

Normal human volunteers 18–65 years of age are used in these studies. Compositions to be tested for vasoconstricting activity are applied to the forearms so that four sites on each arm are treated with 10 mg or 10 microliters of the formulation. This is applied to a 3 cm² area. The sites are varied randomly with regard to the formulations applied. The forearms are wrapped with occlusive film (Saran Wrap ®) for 16 hours. The film is then removed and the arms washed with soap and water. Two hours after the removal of the Saran Wrap ®, the arms are read for vasoconstriction. The reader does not know which formulations were applied to which sites.

The vasoconstrictor assay predicts the clinical effectiveness of pharmacological agents in psoriasis and eczematous diseases of the skin. It is a standard test used to develop agents for topical control of cutaneous inflammatory diseases including psoriasis. See, for example, the following references:

1. Cornell, R. C. and Stoughton, R. B.: Correlation of the vasoconstriction assay and clinical activity in psoriasis. Arch. Dermatol. 121:63–67, 1985.
2. Stoughton, R. B.: Bioassay system for formulations of topically applied glucocorticosteroids. Arch. Dermatol. 106:825–827, 1972.
3. Barry, B. S., Woodford, R.: Activity and bioavailability of topical steroids: In vivo/in vitro correlations for the vasoconstrictor test. J. Clin. Pharmacol. 3:43–65, 1978.
4. Poulsen, B. J., Burdick, K., Bessler, S.: Paired comparison vasoconstrictor assays. Arch. Dermatol. 109:367–371, 1974.
5. McKenzie, A. W., Stoughton, R. B.: Method for comparing percutaneous absorption of steroids. Arch. Dermatol. 86:608–610, 1962.

Two separate studies were carried out with the results of the vasoconstrictor assay in each summarized in Table 1 and Table 2 below.

1-n-heptylazacyclopentan-2-one
1-n-octylazacyclopentan-2-one
1-n-nonylazacyclopentan-2-one
1-n-decylazacyclopentan-2-one
1-n-dodecylazacyclopentan-2-one
1-methylazacycloheptan-2-one
1-n-propylazacycloheptan-2-one
1-n-butylazacycloheptan-2-one
1-n-pentylazacycloheptan-2-one
1-n-hexylazacycloheptan-2-one
1-n-heptylazacycloheptan-2-one
1-n-octylazacycloheptan-2-one
1-n-nonylazacycloheptan-2-one
1-n-decylazacycloheptan-2-one
1-n-butylazacyclononan-2-one
1-n-octylazacyclononan-2-one
1-phenylazacyclopentan-2-one
1-benzylazacyclopentan-2-one
1-(2-chlorophenyl)azacyclopentan-2-one
1,3-Bis-(1-azacyclopentan-2onyl)propane
1,6-Bis-(1-azacyclopentan-2-onyl)hexane Comparable results are obtained.

EXAMPLE 4

Example 2 is repeated except that 26-hydroxycholesterol is replaced with an equal amount of the following compounds:

cholest-5-ene-3-ol-26-formyl-16-one
cholest-4-ene-26-ol-3-one
3 keto-cholest-1,4-dien-26-oic acid
cholest-5-ene-3 beta, 26-diol-16-one (26-hydroxycholesterol-16-one
cholest-4-ene-26-ol-3,16-dione

TABLE 1

| Formulation | Vasoconstrictor Test (Anti-inflammatory Effect) | | | | | | | | | | |
|---|---|---|---|---|---|---|---|---|---|---|---|
| | Subjects' Scores | | | | | | | | | | Total |
| 16-ketocholesterol 1% in 1% Azone ® in ethanol | 0 | 0 | 0 | 0 | 0 | 0 | 0 | 0 | 0 | 0 | 0 |
| 16-ketocholesterol 5% in 5% Azone ® in ethanol | 0 | 0 | 0 | 0 | 0 | 0 | 0 | 0 | 0 | 0 | 0 |
| 26-hydroxycholesterol 5% in 4% Azone ® in ethanol | 0 | 1 | 0 | 0 | 1 | 1 | 0 | 0 | 1 | 0 | 4 |
| 26-hydroxycholesterol 1% in 1% Azone ® in ethanol | 0 | 1 | 0 | 0 | 0 | 0 | 0 | 0 | 0 | 0 | 2 |
| Hydrocortisone 0.5% in ethanol | 0 | 1 | 0 | 0 | 0 | 0 | 1 | 0 | 0 | 0 | 2 |
| Hydrocortisone 1.0% in ethanol | 1 | 1 | 0 | 1 | 0 | 1 | 1 | 1 | 1 | 1 | 8 |

0 = no vasoconstriction
1 = mild vasoconstriction
2 = moderate vasoconstriction
Note that 26-hydroxycholesterol was active in this assay, while 16-ketocholesterol which does not have a hydroxy, keto or carboxylic acid group at the 26 position was inactive.

TABLE 2

| Formulation | Vasoconstrictor Test (Anti-Inflammatory Effect) | | | | | | | | | | |
|---|---|---|---|---|---|---|---|---|---|---|---|
| | Subjects' Scores | | | | | | | | | | Total |
| Cholest-1,4-diene-26-ol-3-one (1%) in 0.8% Azone ® in ethanol | 2 | 1 | 1 | 0 | 0 | 0 | 0 | 1 | 1 | 0 | 6 |
| Cholest-1,4-diene-26-ol-3-one (5%) in 4% Azone ® in ethanol | 1 | 0 | 1 | 1 | 1 | 0 | 0 | 0 | 0 | 0 | 4 |
| Hydrocortisone (1%) in ethanol | 1 | 1 | 0 | 0 | 0 | 1 | 1 | 0 | 0 | 1 | 5 |
| Hydrocortisone (0.2%) in ethanol | 0 | 1 | 0 | 0 | 0 | 0 | 0 | 0 | 0 | 0 | 1 |

0 = No vasoconstriction
1 = Mild vasoconstriction
2 = Moderate vasoconstriction
Note again an oxygenated cholesterol derivative having a hydroxy group in the 26 position shows activity in the above assay.

EXAMPLE 3

Example 2 is repeated, except the 1-n-dodecylazacycloheptan-2-one is replaced with an equal amount of each of the following compounds:
1-n-hexylazacyclopentan-2-one cholest-1,4-diene-26-ol-3, 16-dione
3,16-diketo-cholest-1,4-dien-26-oic acid Comparable results are obtained.

It should be understood that various changes may be made in carrying out the above method and in the composition set forth above without departing from the spirit and scope of the invention. It is intended that all matter contained in the above description shall be interpreted as illustrative and not limiting.

We claim:

1. A method for treating an animal suffering from a proliferative or inflammatory skin disease comprising topically administering to the skin of said animal an amount of an oxygenated chlolesterol having a hydroxy, keto or carboxylic acid in the 26 position or a pharmaceutically acceptable derivative thereof containing said hydroxy, keto or carboxylic acid in the 26 position, effective to treat said proliferative or inflammatory skin disease.

2. The method of claim 1 wherein said oxygenated cholesterol is selected from the group consisting of:
cholest-5-ene-3-ol-26-formyl-16-one,
cholest-4-ene-26-ol-3-one,
cholest-1,4-diene-26-ol-3-one,
3 keto-cholest-1,4-dien-26-oic acid,
cholest-5-ene-3 beta, 26-diol, 16-one (26-hydroxycholesterol-16-one),
cholest-4-ene-26-ol-3,16-dione,
cholest-1,4-diene-26-ol-3, 16-dione,
3,16-diketo-cholest-1,4-dien-26-oic acid, and
26-hydroxycholesterol, 3. The method of claim 2 wherein said oxygenated holesterol is 26-hydroxycholesterol.

4. The method of claim 2 wherein said oxygenated cholesterol is cholest-1,4-diene-26-ol-3-one.

5. The method of claim 1 wherein said oxygenated cholesterol is administered in combination with a penetration-enhancing compound.

6. The method of claim 5 wherein said penetration-enhancing compound is selected from the group of compounds represented by the structural formula:

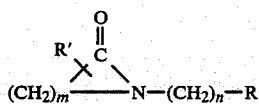

wherein R' is H or a lower alkyl group, m is 3–7, n is 0–17 and R is —CH$_3$, phenyl or substituted phenyl or

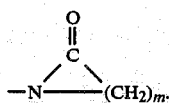

7. The method of claim 6 wherein when m is b 3 and R is —CH$_3$, then n is not 0–6.

8. The method of claim 7 wherein said penetration enhancing-compound is 1-n-dodecylazacycloheptan-2-one.

9. The method of claim 8 wherein said oxygenated cholesterol is 26-hydroxycholesterol.

10. The method of claim 8 wherein said oxygenated cholesterol is cholest-1,4-diene-26-ol-3-one.

11. The method of claim 1 wherein said proliferative skin disease is psoriasis.

12. The method of claim 9 wherein said disease is psoriasis.

13. The method of claim 10 wherein said disease is psoriasis.

14. A method of treating a patient suffering from a porliferative or inflammatory skin disease characterized by vasodilation and reddening of the skin, comprising applying to the effected skin a therapeutic composition comprising a therapeutically effective amount for enhancing vasoconstriction and decreasing proliferation or inflammation of the skin, of an oxygenated cholesterol having a hydroxy, keto or carboxylic acid group in the 26 position or a pharmaeutically effective derivative thereof containing said hydroxy, keto or carboxylic acid in the 26 position, and a pharmaceutically acceptable carrier therefor.

15. A topical composition comprising an oxygenated cholesterol having a hydroxy, keto or carboxyli acid substituent in the 26 position or a pharmaceutically acceptable derivative thereof containing said hydroxy, keto or carboxylic acid in the 26 position, and a pharmaceutically acceptable carrier in the form of an ointment, lotion, paste, jelly, spray, aerosol, or bath oil for said oxygenated cholesterol.

16. The composition of claim 15 wherein said oxygenated holesterol is selected from the group consisting of:
cholest-5-ene-3-ol-26-formyl-16-one,
cholest-4-ene-26-ol-3-one,
cholest-1,4-diene-26-ol-3-one,
3 keto-cholest-1,4-dien-26-oic acid,
cholest-5-ene-3-beta, 26-diol16-one (26-hydroxycholesterol-16-one),
cholest-4-ene-26-ol-3,16-dione,
cholest-1,4-diene-26-ol-3, 16-dione,
3,16-diketo-cholest-1,4-dien-26-oic acid, and
26-hydroxycholesterol.

17. The compostion of claim 16 wherein said oxygenated cholesterol is 26-hydroxycholesterol.

18. The composition of claim 17 wherein said oxygenated cholesterol is cholest-1,4-diene-26-ol-3-one.

19. The composition of claim 15 further comprising a penetration-enhancing compound.

20. The composition of claim 19 wherein said penetration-enhancing compound is selected from the group of compounds represented by the structural formula:

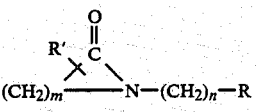

wherein R' is H or a lower alkyl group, m is 3–7, n is 0–17 and R is —CH$_3$, phenyl or substituted phenyl or

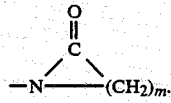

21. The composition of claim 20 wherein when m is 3 and R is —CH$_3$, then n is not 0–6.

22. The composition of claim 21 wherein said penetration enhancing-compound is 1-n-dodecylazacycloheptan-2-one.

23. The composition of claim 22 wherein said oxygenated cholesterol is 26-hydroxycholesterol.

24. The composition of claim 22 wherein said oxygenated cholesterol is cholest-1,4-diene-26-ol-3-one.

* * * * *